(12) United States Patent
Bomgaars et al.

(10) Patent No.: US 6,695,272 B1
(45) Date of Patent: Feb. 24, 2004

(54) DRINK COASTER AND AIR FRESHENER

(76) Inventors: Gregory Jay Bomgaars, Suds Factory, 9171 E. Westview Rd., Littleton, CO (US) 80124; Robert Anthony Terranova, 327 Cherry St., Castle Rock, CO (US) 80104

( * ) Notice: Subject to any disclaimer, the term of this patent is extended or adjusted under 35 U.S.C. 154(b) by 0 days.

(21) Appl. No.: 10/080,227

(22) Filed: Feb. 21, 2002

(51) Int. Cl.[7] .............................................. B65D 19/00
(52) U.S. Cl. ........................... 248/346.11; 248/346.01; 239/53; 428/157
(58) Field of Search ................. 248/346.11, 346.01; 215/394, 393; 239/53, 56; 428/157

(56) References Cited

U.S. PATENT DOCUMENTS

| | | | |
|---|---|---|---|
| 2,014,268 A | | 9/1935 | Tenney |
| 2,303,073 A | * | 11/1942 | Brown .......................... 239/53 |
| 3,017,051 A | * | 1/1962 | Rosenfeld .............. 248/346.11 |
| 3,195,847 A | * | 7/1965 | Squires .................. 248/346.11 |
| 3,268,198 A | * | 8/1966 | Swett ..................... 248/346.11 |
| 4,089,498 A | * | 5/1978 | Woodruff ............... 248/346.11 |
| 4,158,440 A | * | 6/1979 | Sullivan et al. ................. 239/6 |
| 4,206,570 A | * | 6/1980 | Cooper ............................ 47/71 |
| 4,858,872 A | * | 8/1989 | Witt ....................... 248/346.11 |
| 4,953,823 A | * | 9/1990 | Sheaffer et al. ........ 248/346.11 |
| 4,978,566 A | * | 12/1990 | Scheurer et al. ............. 428/157 |
| 5,000,413 A | | 3/1991 | Kawashima |
| 5,004,138 A | | 4/1991 | Gabas |
| 5,018,695 A | * | 5/1991 | Bishop .................. 248/346.11 |
| 5,172,937 A | * | 12/1992 | Sachetti ........................ 283/81 |
| 5,273,182 A | | 12/1993 | Laybourne |
| 5,304,358 A | * | 4/1994 | Hoyt et al. ................... 422/305 |
| 5,395,047 A | * | 3/1995 | Pendergrass, Jr. ............ 239/56 |
| D357,388 S | * | 4/1995 | Gaffin .......................... D7/625 |
| 5,413,302 A | * | 5/1995 | Ferster .................. 248/346.11 |
| 5,533,697 A | * | 7/1996 | Fletcher et al. ............. 248/146 |
| 5,695,270 A | | 12/1997 | Collet |
| 5,738,831 A | * | 4/1998 | Bethel ......................... 422/120 |
| 5,775,659 A | * | 7/1998 | Hartlaub et al. ........ 248/346.11 |
| 5,899,382 A | * | 5/1999 | Hayes et al. ................... 239/56 |
| 5,938,162 A | * | 8/1999 | Honjo ................... 248/346.11 |
| 5,997,995 A | * | 12/1999 | Scianna ....................... 428/195 |
| 6,082,866 A | * | 7/2000 | Amedee ....................... 362/34 |
| 6,322,033 B1 | * | 11/2001 | Lee ....................... 248/346.01 |
| 6,328,287 B2 | * | 12/2001 | Wittek .......................... 261/30 |
| 6,367,706 B1 | * | 4/2002 | Putz .............................. 239/6 |
| 2002/0023886 A1 | * | 2/2002 | Lewis .......................... 211/40 |

FOREIGN PATENT DOCUMENTS

GB          2149349 A    *   6/1985

OTHER PUBLICATIONS

Origin Associates Pte Ltd, Family Day Gifts, Copyright 2001 (Scented Rubberised Coaster).*

* cited by examiner

*Primary Examiner*—Anita King
(74) *Attorney, Agent, or Firm*—Henry L. Smith, Jr.

(57) ABSTRACT

The invention is a disk-shaped combination drink coaster and air freshener for a drink holder. The top layer absorbs condensation or liquid spills from a drink container. The disk may have a layer impregnated with an air freshener, which will gradually be released into the vehicle or room. The disk has a plurality of layers designed to absorb liquid spills and prevent liquid spills and the air freshener material from leaving deposits on the bottom of the drink holder. The device may be imprinted with advertising names or symbols. The device has perforations to facilitate tearing off part of the circumference of the disk to reduce its diameter. The disk can also be used in combination with a coaster holder impregnated with air freshener, the weight of which prevents the coaster and air freshener from sticking to the bottom of a liquid container when the container is lifted.

29 Claims, 6 Drawing Sheets

Top View

Side View

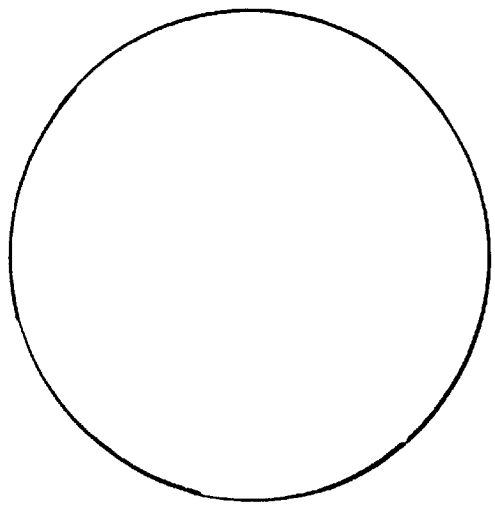
Top View
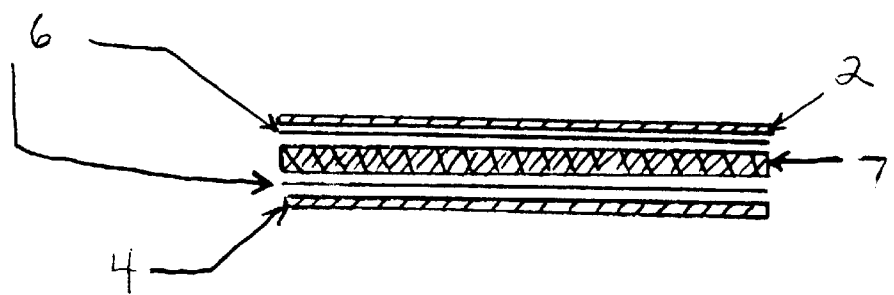
SIDE VIEW
Fig. 5

DRINK COASTER AND AIR FRESHENER

BACKGROUND

1. Field of Invention

The invention relates to a device for containing spills and drips from cups or liquid containers placed in the drink holder of a vehicle or at a casino, sporting facility, or the like, and at the same time providing an air freshening effect to overcome the effect of tobacco smoke or overcome odors from foods or spilled liquids. The invention could be used by individual vehicle owners, or more commonly in the vehicle wash industry when a vehicle owner takes the vehicle to a wash facility where the outside and inside of the vehicle are cleaned.

2. Description of Prior Art

The problem of catching condensation and drips from drink containers has been dealt with over the years by prior art. A number of patents have focused on preventing drips and spills from drink containers. Representative of this art is U.S. Pat. No. 2,014,268 to V. Tenney, Sep. 10, 1935. This patent discloses a coaster for a drink glass to be used on a table or similar surface. U.S. Pat. No. 4,206,570 to William Cooper, Jun. 10, 1980, discloses a device for supporting a vessel containing liquid, comprising a liquid impervious base and a liquid absorbent layer. The Applicant is not aware of coasters designed for use in the drink holder of vehicles, casinos, or recreation facilities. The problem of removing odors from vehicles has been addressed by positioning scent-emitting objects in vehicles including, currently, a small, flat, tree-shaped object suggestive of an evergreen tree, which is hung from the rear view mirror of the vehicle. Representative of this air freshening art for vehicles are U.S. Pat. No. 4,352,461, to P. N. Orta, Oct. 5, 1982 and U.S. Pat. No. 5,004,138 to C. Gabas, Apr. 2, 1991. The latter patent discloses a combination of an automobile sun visor with a built-in air freshener box. The Applicant is not aware of a device which would simultaneously act as a drink coaster and air freshener.

SUMMARY OF INVENTION

The invention is a combination drink container coaster and air freshener generally shaped like a flat circular disk, and shaped so as to be insertable into a drink holder. Such drink holders are commonly provided in modern automobiles and trucks, typically in the front seat area of the vehicle between the two front seat positions. They are also sometimes provided in casinos near gambling machines, and near seats at recreational facilities. The invention is placed in the bottom of the drink holder to catch drips from the drink container which would otherwise stain or leave residue in the bottom of the drink holder. The device is also impregnated with an air freshener, typically a somewhat oily liquid. The device has a hole in the top layer near the circumference of the disk to facilitate removal from the drink holder when a pointed instrument is positioned in the hole. One or more circular lines of perforations are incorporated parallel to the circumference of the disk so that excess material can be torn off when not needed in order that the device can fit into smaller drink holders. The disk could comprise several layers of various materials in various combinations, attached to each other by various means. The preferred embodiment of the invention would comprise a top layer of absorbent paper, cardboard, or similar material, followed by a layer of waxed paper, or other liquid impervious paper or plastic, followed by a layer of pulp paper or similar material which is impregnated with an air freshener liquid typically having a thick and oily consistency. Beneath that is another layer of waxed paper or other liquid impervious paper or plastic, and beneath that is a final layer of absorbent paper or cardboard or similar material.

OBJECTS AND ADVANTAGES

The objects of the present invention are:
1. To absorb condensation and drips from drink containers used by occupants of a vehicle, casino, or recreation facility in order to avoid leaving a stain or residue in the drink holder.
2. To provide an air freshening effect in a vehicle or room to counteract the odor of tobacco smoke, odors from drinks or foods, or any other odors which may be present in the vehicle or room.
3. To prevent the air freshening liquid or oil contained in the invention from leaking out and staining or leaving a residue on the bottom of the drink container, or drink holder.
4. To provide individuals or vehicle wash companies an easy-to-use device to both catch liquid drips from drink containers and at the same time freshen the air in a vehicle.
5. To provide carwash companies, casinos, or sporting event facilities and the like a way to provide an inexpensive complimentary gift to their customers when their customers patronize the location.
6. To provide carwash or other companies a device for advertising and carrying their name or logo in the vehicle to remind customers of the benefits from the company, and to remind customers to take advantage of the services of the company again.
7. To provide an inexpensive and inconspicuous source of air freshening effect for a vehicle or room.
8. To provide a source of air freshening effect for a vehicle without hanging objects in the vehicle which may distract the driver or interfere with his vision.
9. To provide an inexpensive and easily replaceable device for simultaneously absorbing drink spills and providing air freshening effect.
10. To provide a device which is easy and cheap to manufacture.
11. To provide a device which is easily adapted to drink holders of varying sizes, by tearing off a part of the circumference of the device so that it easily fits into the bottom of drink holders of varying sizes.
12. To provide a device which is easily removed from the bottoms of deep drink holders by positioning a pointed object in the hole near the circumference of the device, so that it can be easily lifted from the bottom of the drink holder.
13. To provide a coaster holder which can be used in combination with the coaster and air freshener, which because of its weight, may reduce the likelihood that the coaster and air freshener would stick to the bottom of a drink container when the container is lifted by a person.
14. To provide a coaster holder which may be made of an attractive color to match the interior of the vehicle or to be otherwise attractive to the vehicle occupants.
15. To provide a coaster holder which may have scent impregnated into the plastic of the coaster holder.

Still further objects and advantages will become evident from the detailed description of the invention, and the drawings.

DRAWING FIGURES

FIG. 5 is a side cross-sectional view of the device showing the various layers of materials comprising the device, and the Figure also shows a top view of the device without the removal hole.

Figure 1:
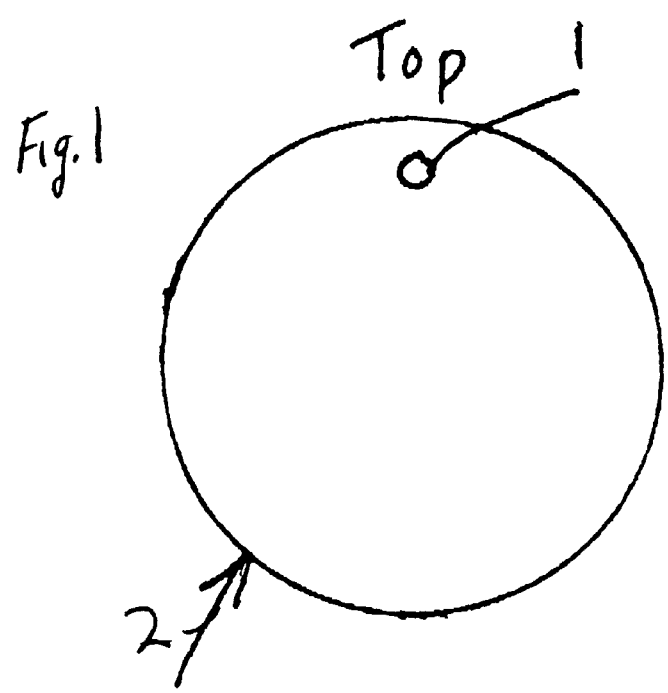
FIG. 1 is a top view of the device showing the top layer and the removal hole near the circumference of the disk.

REFERENCE NUMERALS IN DRAWINGS 1 removal hole
2 top layer
3 logo
4 bottom layer
5 perforations
6 liquid impervious layer
7 air freshener layer
8 coaster holder
9 coaster holder hole
10 coaster retainer means
11 annular surface
12 raised rim

DETAILED DESCRIPTION OF THE DRAWINGS

FIG. 1 is a top view of the device showing the removal hole 1 near the circumference of the device and top layer 2, which is a liquid absorbent means. The hole allows a pointed instrument to be inserted into the hole so that the disk can be lifted out of the drink holder. Top layer 2 comprises cardboard or similar absorbent material for absorbing condensation or spills from the drink container.

Figure 2:
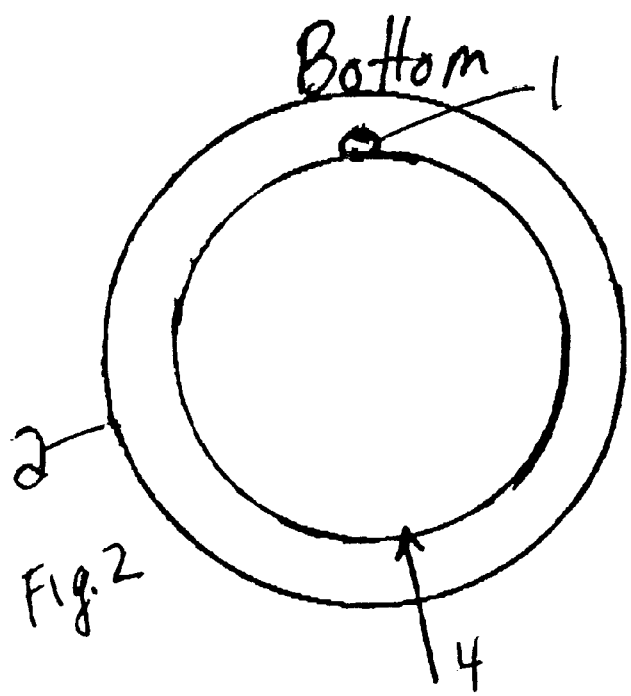
FIG. 2 is a bottom view of the device showing the removal hole and the bottom layer which is typically smaller than the top layer.

FIG. 2 is a bottom view of the device showing removal hole 1, top layer 2, and bottom layer 4 which is typically smaller than top layer 2 in order to better catch spills from the drink container positioned on top of top layer 2. Air freshener layer 7 is positioned between bottom layer 4 and top layer 2, but is not visible in this figure.

Figure 3:
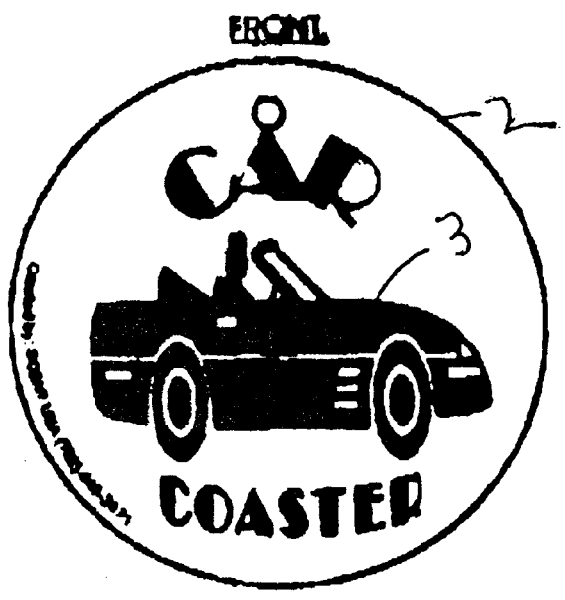
FIG. 3 is a top view of the device showing an advertising logo imprinted on the top layer.

FIG. 3 shows a logo or other advertising name, or symbol 3 printed on the top layer 2.

Figure 4:
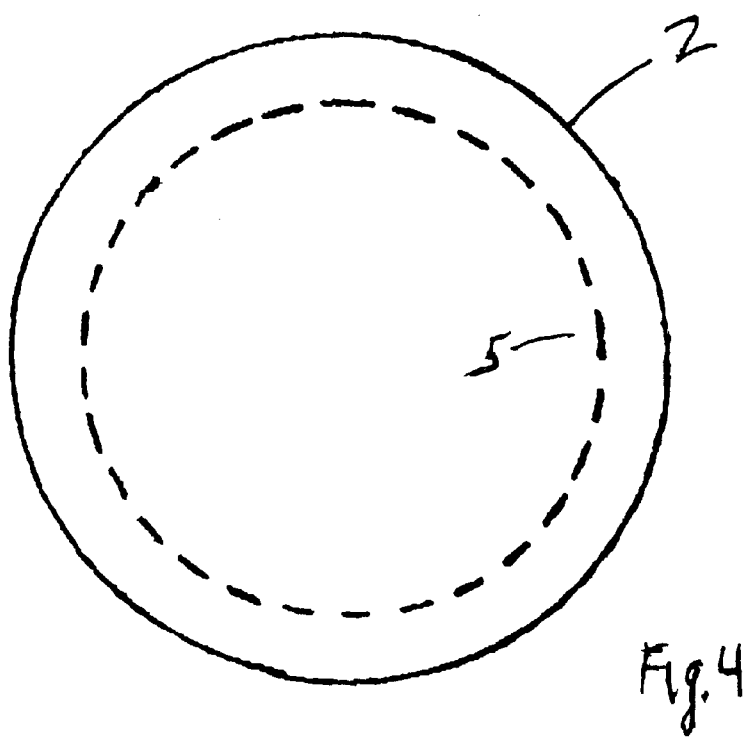
FIG. 4 is a top view of the device showing circular lines of perforations by means of which an outer ring of material can be torn off to produce a smaller size disk.

FIG. 4 is a top view of the device showing top layer 2 containing a line of perforations 5 around the circumference of the device. The outside portion of the disk can be torn away from the inside portion by severing perforations 5, thus adapting the device to fit into smaller drink holders.

FIG. 5 is a cross-sectional view of the device showing the various layers comprising the device. Top layer 2 typically comprises cardboard or similar material for absorbing condensation or drink spills. Attached to top layer 2 is impervious layer 6 comprising wax paper, plastic, glue, or similar material impervious to liquid. This layer prevents liquid from the drink holder from moving downward into the device and thus spreading to the air freshener layer or the bottom of the drink holder. It also prevents the air freshener oily liquid from contaminating the top layer 2 and the bottom of the drink container, which rests on top layer 2. Air freshener layer 7, which is one air freshener holder means, typically comprises a layer of cardboard or similar material which has been impregnated with an air freshener means typically a thick oily liquid or chemical which slowly vaporizes and thus releases inside the vehicle or room a pleasant air freshening odor which counteracts or masks any unpleasant odor which may be in the vehicle or room. Beneath air freshener layer 7, is another liquid impervious layer 6. This layer prevents the oily air freshener liquid from moving downward and staining or leaving a residue on the bottom of the drink holder. The bottom layer 4 is another layer of cardboard or similar material which can absorb any drink spills or condensation which is not absorbed by top layer 2. In addition, bottom layer 4 would absorb any air freshener liquid which would leak out of air freshener layer 7 and thus stain the bottom of the drink holder which would be in contact with bottom layer 4.

Figure 6:
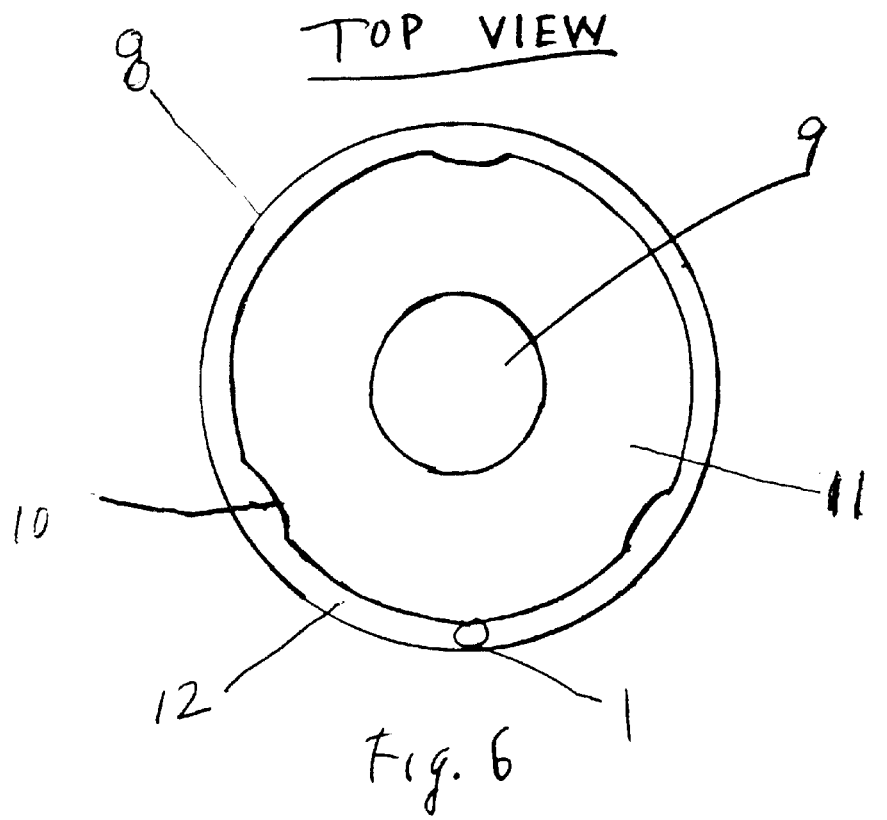
FIG. 6 shows the coaster holder 8 adapted to receive the coaster and air freshener disk, and to hold it in place.
Figure 7:
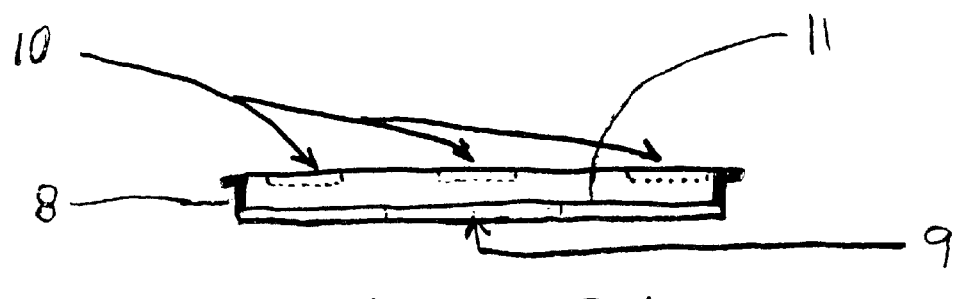
FIG. 7 is a side view of the coaster holder in FIG. 6.

FIG. 6 is a top view of the coaster holder 8. It shows the coaster holder hole 9 which allows the coaster and air freshener disk to be popped out and replaced, by pressing a user's finger through the hole. The coaster retainer means 10 is also shown as well as removal hole 1 and raised rim 12. The coaster retainer means 10 is typically a larger place in the rim of the coaster holder 8 which extends over the annular surface 11 and holds the coaster and air freshener disk inside the coaster holder. The coaster and air freshener disk is inserted in the coaster holder by slipping the edge of it under one retainer means 10, and then popping another edge under one or more other retainer means 10. FIG. 6 also shows the removal hole 1, which can receive an elongated pointed object to facilitate removal of the coaster holder from deeper drink holder cavities. FIG. 7 is a side view of the coaster holder in FIG. 6 showing how the retainer means 10 project somewhat over the space occupied by the coaster and air freshener disk. FIG. 7 also shows the coaster holder hole 9 which extends completely through the coaster holder. When the coaster and air freshener disk is inserted into the coaster holder 8, it is held in position between coaster retainer means 10 and raised rim 12 and the annular surface 11, which is the inside bottom surface of the coaster holder 8. The coaster and air freshener disk can be removed from the coaster holder by placing a finger in coaster holder hole 9 and pressing the finger through the hole, which will cause the coaster and air freshener disk to pop out from under retainer means 10, and thus be freed from the coaster holder.

DESCRIPTION-PREFERRED EMBODIMENT

In the preferred embodiment, the line of perforations 5 would be present to enable the device to be adapted to different size drink holders. This is one diameter reducing means. The top layer 2 would be comprised of cardboard for adsorbing liquid spills. Impervious layer 6 would be comprised of waxed paper or plastic. Air freshen layer 7 would be comprised of pulp paper impregnated with an air freshening liquid. Bottom layer 4 would also be comprised of cardboard. A logo or advertising name or slogan 3 would be imprinted on top layer 2. Top layer 2 would be larger in diameter than bottom layer 4 to reduce the likelihood that spilled liquid would move downward beyond top layer 2 and thereby contaminate air freshener layer 7 or bottom layer 4, or come into contact with or stain the bottom of the drink holder. In the preferred embodiment, the removal hole 1 is present near the circumference of the disk so that a pointed object can be inserted in the hole, so that the pointed object can easily remove the device from the bottom of deeper drink holders. In the preferred embodiment, the various layers can be attached to each other by glue or various adhesives or other attaching means known to those skilled in the art.

OPERATION OF THE INVENTION

The operation of the invention is as follows. The device is positioned with the smaller bottom layer 4 toward the bottom of the drink holder. The device is then lowered into the bottom of the drink holder. The device then visibly displays the logo or advertisement to the occupants of the vehicle or room. When the occupant of the vehicle or room places a drink container into the drink holder, the bottom of the drink container comes into contact with the top layer 2 of the device, and rests on this layer. Any condensation on the bottom of the drink container or any spill of the drink liquid which has moved down the side of the drink container to the bottom of the drink container would be absorbed by the top layer 2 of the device. If a large amount of spilled liquid or condensation happens to move downward over the edge of top layer 2, it is very likely to be absorbed by the exposed bottom portion of top layer 2. With the device in position in the bottom of the drink holder, the air freshener liquid can slowly evaporate into the vehicle or room thus counteracting or masking unpleasant odors such as tobacco smoke, food odors, etc. The scent of the air freshener is selected to be pleasant to vehicle or room occupants and, in the case of a vehicle, to reinforce the impression that the car has been cleaned inside and out by the carwash company. If the drink holder is small, an outer ring-shaped portion of top layer 2 can be torn away along perforations 5 and discarded, thus producing a device of smaller diameter which can fit into the smaller drink holder. Because of the liquid impervious layers 6, the air freshener liquid impregnated in air freshener layer 7 cannot move downward and contaminate bottom layer 4 and from there stain or leave an oily residue on the bottom of the drink holder. Also, the air freshener liquid cannot move upward and contaminate top layer 2 and the bottom of the drink container. Likewise, if top layer 2 becomes excessively saturated with spilled liquid, the liquid impervious layers 6 would prevent the spilled liquid from moving downward and contaminating bottom layer 4 or leaving a stain or residue on the bottom of the drink holder which is in contact with bottom layer 4.

The air freshener liquid impregnated in air freshener layer 7 would escape from the layer and vaporize slowly because of the limited exposed surface of air freshener layer 7, namely the small cylindrical area around the device defined by the exposed edge of the air freshener layer 7. In this way, the air freshener liquid would not evaporate too fast and produce an excessively strong odor in the vehicle or room. Likewise, because of the slow of evaporation rate of the air freshener liquid, the evaporation of the liquid would continue for a relatively prolonged period of time, thus providing a beneficial air freshening effect over a relatively long period of time. In the case of a vehicle, at the next carwash, or whenever it is desirable to replace the device, the device can be easily removed by insertion of a pointed object into removal hole 1. The pointed object can then easily lift the device out of deeper drink holders while the pointed object is kept positioned in the hole and positioned near or against the inside generally cylindrical surface of the drink holder. A new device can be easily positioned in the drink holder in order to absorb drinks spills with new absorbent capacity, and to provide a renewed air freshener effect.

The operation of the drink coaster and air freshener in conjunction with the coaster holder 8 is described above in the descriptions of FIGS. 6 and 7.

TESTS

A number of tests have proven that the device can adequately absorb drink spills and prevent depositing residue on the bottom of the drink holder or staining the drink holder. Likewise tests have demonstrated a prolonged air freshening effect from the slow escape rate of the air freshening liquid into the vehicle or room. In addition, the device prevents the air freshening liquid from coming into contact with and staining the bottom of the drink holder, or contaminating the bottom of the drink container. Tests have also demonstrated that the device can be easily removed from the drink holder by inserting a pointed object into the removal hole 1. Likewise, tests have shown that the device can be easily adapted to smaller drink holders by tearing off the ring-shaped portion of the device along the lines of perforations 5. Tests have also demonstrated that the coaster holder, because of its weight, greatly reduces the likelihood that the coaster and air freshener disk will stick to the bottom of the liquid container when the liquid container is lifted by a person.

ADDITIONAL EMBODIMENTS

Additional embodiments of the invention could comprise, as attaching means for attaching the liquid adsorbent means and the air freshener holder means, different glues or adhesives for attaching the various layers to each other, or possibly heat-bonding processes whereby liquid impervious layers 6 could be bonded to top layer 2 and bottom layer 4 and air freshener layer 7.

Other materials, as absorbent means, besides cardboard could be used for top layer 2 and bottom layer 4, such as various fibrous or sponge-like materials, either natural or artificial. For liquid impervious layers 6 or attaching means, other materials might be used in addition to plastic or waxed paper, such as dense plastic foam layers. Liquid impervious layers 6 or attaching means could be formed by spraying various plastics dissolved in suitable solvents which will evaporate during the spraying process. Such plastics and solvents are known to those skilled in the art. Separate liquid impervious layers 6 might be omitted in some embodiments if a thick uniform liquid impervious layer of glue or adhesive was substituted for these layers. As air freshener holder means, the air freshener layer 7 in addition to cardboard could be made of various fibrous, sponge-like, or plastic foam materials, provided that the air freshener liquid could migrate between the cells of plastic foam materials. Obviously, as air freshener means, a multitude of air freshener liquids or solids are possible, depending on the scent desired. The liquids or solids could be selected based on how rapidly they evaporate or how viscous they are, the latter being important to prevent leakage of air freshener liquid out of air freshener layer 7. The device could be produced in a number of diameters and thicknesses adapted to fit inside drink holders of many sizes and depths, and with different capacities for absorbing liquid spills, and different capacities for releasing the air freshener liquid. In addition, the device could be produced with various diameter reducing means such as a number of concentric rings of perforations or lines of weakness 5, so that one or more ring-shaped portions of the device could be torn away along perforations 5 to produce devices of several different diameters adapted to fit a number of drink holder sizes. In addition, the logos 3 could be printed on the device in various colors of ink including, inks which would glow in a darkened vehicle thus calling attention to the advertising logo and making it easier for the vehicle occupants to find the vehicle drink holder in the dark. These glow-in-the-dark inks could contain various glow in the dark means such as luminescent chemical compounds known to those skilled in the art, including calcium sulfide. Alternatively, the logos could be formed on the top layers of the device by a process of embossing the logos under pressure into the top layer 2 typically made of cardboard, by processes known to those skilled in the art.

In summary, various attaching means known to those skilled in the art for attaching the various layers of the device to each other could be used in addition to glues, adhesives or heat and pressure bonding. The top layer 2 and bottom layer 4, and air freshener layer 7 could comprise other absorbent means in addition to cardboard, fibrous materials, or foam-like materials.

The coaster and air freshener disk can be used alone or in combination with the coaster holder 8. The coaster holder 8, as shown in FIGS. 6 and 7, would typically be circular in shape to match the generally circular drink holder cavities; however, coaster holder 8 could be in the shape of various polygons. The coaster holder 8 could be made from many different materials including metal, plastic, high-density plastic foam or many other reasonably rigid materials. The coaster holder 8 could have the same color as, or a complementary color to, the interior of the vehicle or room, or alternatively could be black, white, silver or gold. In addition to the decorative aspect of the coaster holder, the coaster holder provides the additional function of preventing the coaster and air freshener disk from sticking to the bottom of the liquid container when the container is lifted by a person. This sticking may occur because of moisture on the bottom of the liquid container or sticky liquid which has spilled from the liquid container, or possibly because of the heat of the liquid in the liquid container. The added weight provided to the coaster and air freshener disk by the coaster holder substantially reduces the likelihood that the disk will stick to the bottom of the liquid container when the liquid container is raised by a person. The coaster holder could be made of a plastic which contains a glow in the dark means such as calcium sulfide or other luminescent compounds known to those skilled in the art.

The coaster retainer means 10 may be various shaped projections extending from the raised rim 12 of the coaster holder 8 a short distance above the annular surface 11. The shape of these projections could include a segment of a circle, rectangle, triangle, etc. As discussed above, when the coaster and air freshener disk is used alone in a drink holder, the ring of perforations can be used to adjust to disk to drink holders of various sizes. Likewise, when the coaster and air freshener disk is used in combination with the coaster holder, the ring of perforations on the coaster and air freshener disk can be used to adjust the size of the disk to the size of the coaster holder. In another embodiment, the air freshener layer 7 and one liquid impervious layer 6 could be omitted if the air freshener material is impregnated into the material forming the coaster holder, such as plastic. Obviously, the air freshener coaster device could also be used on ordinary flat surfaces, such as tables, bars, etc.

CONCLUSIONS, RAMIFICATIONS AND SCOPE

A number of changes are possible to the materials and methods described above, while still remaining within the scope and spirit of the invention. Various liquid absorbent means could be used in the top layer 2 and bottom layer 4 for absorbing spilled liquids, such as cardboard, pulp board, blotter paper, pulp paper, natural sponge, plastic foam or matted fibers, and other similar means known to those skilled in the art. The air freshener holder means in layer 7 could be made of many different materials, including those in the preceding sentence. The air freshener means could include a very wide variety of liquids or solids known to those skilled in the art which provide a pleasant scent or which mask certain odors. The diameter reducing means could include lines of perforations of various shapes, lines of weakness in circular or other configurations; it could also include wedge-shaped breakable portions along the circumference of the disk. The disk removal means could comprise a hook, tab or string attached to the device, in addition to a hole to receive a pointed object. Some of the many variations and alternate embodiments possible for this invention are discussed above. Those skilled in the art could produce other variations involving different scents, different materials for the layers and different means of attaching the layers together in a sandwich-like structure.

The specifics about the form of the invention described in this application are not intended to be limiting in scope. The scope of the invention is to be determined by the claims, and their legal equivalents, not the examples given above.

We claim:

1. A device which is, in combination, a drink coaster and air freshener, adapted to be positioned in a drink holder or on a flat surface, comprising a substantially circular or polygonal shaped disk, said disk further comprising a plurality of layers including a top layer and a bottom layer liquid absorbent and an air freshener middle layer impregnated with a material capable of evaporation and selected from a group of substances or mixtures having an odor pleasing to humans or capable of combating odors unpleasant to humans.

2. The device of claim 1, further comprising a removal hole in the disk positioned relatively close to the edge of the disk and adapted for insertion of a pointed object, whereby the disk is capable of being easily removed by the pointed object from said drink holder.

3. The device of claim 2, wherein the layers of the disk beneath the top layer are smaller in circumference than the top layer, whereby spilled liquid from a drink container is less likely to contact the middle and bottom layers of the disk or the bottom of the drink holder.

4. The device of claim 1, wherein the layers of the disk beneath the top layer are smaller in circumference than the top layer, whereby spilled liquid is less likely to contact the middle and bottom layers of the disk or the bottom of said drink holder.

5. The device of claim 4, further comprising a removal hole in the disk positioned relatively close to the edge of the disk and adapted for insertion of a pointed object, whereby the disk is capable of being easily removed by the pointed object from said drink holder.

6. The device of claim 1, wherein the top layer includes one or more sets of substantially circular or polygonal lines of perforations or lines of weakness, inside of, and parallel to, the circumference of said disk, whereby an outer substantially ring-shaped portion of the top layer of said disk can be removed by tearing outer portions of the top layer away from the inside substantially circular or polygonal shaped portion of said disk, and whereby the diameter of said disk can be changed to fit drink holders of varying sizes.

7. The device of claim 6, further comprising a removal hole in the disk positioned relatively close to the edge of the disk but inside the set of perforations or lines of weakness with the smallest diameter, and adapted for insertion of a pointed object, whereby the disk is capable of being easily removed by the pointed object from said drink holder.

8. The device of claim 6, wherein the layers of the disk beneath the top layer are smaller in circumference than the top layer, whereby spilled liquid from a drink container is less likely to contact the bottom layers of the disk or the middle and bottom of the drink holder.

9. The device of claim 6, further comprising a logo, symbol, name, or other advertising or identifying mark printed or embossed on the liquid absorbent top layer of said disk.

10. The device of claim 6, further comprising a removal hole in the disk positioned relatively close to the edge of the disk but inside the set of perforations or lines of weakness with the smallest diameter, and adapted for insertion of a pointed object, whereby the disk is capable of being easily removed by the pointed object from a drink holder, and wherein the layers of the disk beneath the top layer are smaller in circumference than the top layer.

11. The device of claim 1, wherein the air freshener layer impregnated with a material capable of evaporation, has an exposed substantially cylindrical or polygonal edge surface out of which the material can evaporate from the disk, and wherein the top and bottom surfaces of said air freshener layer are sealed by being attached to one or more layers of liquid impervious material.

12. The device of claim 11, wherein the liquid impervious layer comprises waxed paper, plastic, a continuous coating of glue, or a continuous coating of adhesive, or a layer of plastic applied by spraying the plastic dissolved in a solvent capable of evaporation.

13. The device of claim 11, wherein the air freshener layer is comprised of cardboard, pulp board, blotter paper, pulp paper, natural sponge, plastic foam, or matted fibers.

14. The device of claim 6, further comprising a removal hole in the disk positioned relatively close to the edge of the disk and adapted for insertion of a pointed object, whereby the disk is capable of being easily removed by the pointed object from said drink holder.

15. The device of claim 11, wherein the layers of the disk beneath the top layer are smaller in circumference than the top layer, whereby spilled liquid from a drink container is less likely to contact the middle and bottom layers of the disk or the bottom of the drink holder.

16. The device of claim 11, further comprising a logo, symbol, name, or other advertising or identifying mark printed or embossed on the liquid absorbent top layer of said disk.

17. The device of claim 11, wherein the top layer includes one or more sets of substantially circular or polygonal lines of perforations or lines of weakness, inside of, and parallel to, the circumference of said disk, whereby an outer substantially ring-shaped portion of the top layer of said disk can be removed by tearing outer portions of the top layer away from the inside substantially circular or polygonal shaped portion of said disk, and whereby the diameter of said disk can be changed to fit drink holders of varying sizes, and further comprising a removal hole in the disk positioned relatively close to the edge of the disk but inside the set of perforations or lines of weakness with the smallest diameter, and adapted for insertion of a pointed object, whereby the disk is capable of being easily removed by a pointed object from the drink holder, and wherein the layers of the disk beneath the top layer are smaller in circumference than the top layer.

18. The device of claim 1, wherein the liquid absorbent top layer comprises cardboard, pulp board, blotter paper, pulp paper, natural sponge, plastic foam, or matted fibers.

19. The device of claim 1, wherein the bottom layer, beneath the air freshener layer, is comprised of substantially the same material as the liquid absorbent top layer.

20. The device of claim 19, further comprising a logo, symbol, name, or other advertising or identifying mark printed or embossed on the liquid absorbent top layer of said disk.

21. The device of claim 1, further comprising a coaster holder comprising:
(a) a round or polygonal shaped coaster holder disk having a raised rim, adapted to hold the coaster and air freshener, and
(b) a plurality of coaster retainer means extending from the raised rim of the coaster holder over the coaster and air freshener, and adapted to retain the waster and air freshener in a fixed position in the coaster holder disk.

22. The device of claim 21, further comprising a coaster bolder hole through said holder, and a removal hole in the raised rim of the bolder, whereby a human finger or other elongate object can move through the coaster holder hole and press the coaster and air freshener out from the coaster holder, and whereby a pointed object can be inserted in the removal hole, whereby the coaster holder can be removed from a drink holder or similar cavity.

23. The device of claim 22, wherein the coaster holder is made of plastic comprising a glow in the dark means.

24. The device of claim 22, wherein the coaster holder is made of plastic or other moldable material, impregnated with air freshener means, and wherein the air freshener layer is absent.

25. A device which is, in combination, a drink coaster and air freshener, adapted to be positioned in a drink holder, comprising a substantially circular or polygonal shaped disk, said disk further comprising:
(a) a liquid absorbent means,
(b) an air freshener means,
(c) an air freshener holder means,
(d) a diameter reducing means,
(e) a disk removal means, and
(f) an attaching means for attaching parts (a) and (c) together.

26. The device of claim 25, further comprising a coaster holder comprising:
(a) a round or polygonal shaped coaster holder disk having a raised rim, adapted to bold the coaster and air freshener, and
(b) a plurality of coaster retainer means extending from the raised rim of the coaster holder over the coaster and air freshener, and adapted to retain the coaster and air freshener in a fixed position in the coaster bolder.

27. The device of claim 26, further comprising a coaster holder hole through said holder, and a removal hole in the raised rim of the holder, whereby a human finger or other elongate object can move through the coaster holder hole and press the coaster and air freshener out from the coaster holder, and whereby a pointed object can be inserted in the removal hole, whereby the coaster bolder can be removed from a drink holder or similar cavity.

28. The device of claim 27, wherein the coaster holder is made of plastic comprising a glow in the dark means.

29. A device which is, in combination, a drink coaster and air freshener, adapted to be positioned in a drink holder, comprising a substantially circular or polygonal shaped disk, said disk further comprising:
(a) a liquid absorbent means,
(b) a diameter reducing means,
(c) a disk removal means, and
further comprising a coaster holder comprising:
(d) a round or polygonal shaped coaster holder disk having a raised rim, adapted to hold the coaster and air freshener, and
(e) a plurality of coaster retainer means extending from the raised rim of the coaster holder over the coaster and air freshener, and adapted to retain the coaster and air freshener in a fixed position in the coaster holder, wherein the coaster bolder disk is comprised of plastic or other moldable material, impregnated with air freshener means.

* * * * *

UNITED STATES PATENT AND TRADEMARK OFFICE
CERTIFICATE OF CORRECTION

PATENT NO. : 6,695,272 B1
APPLICATION NO. : 10/080227
DATED : February 24, 2004
INVENTOR(S) : Bomgaars et al.

It is certified that error appears in the above-identified patent and that said Letters Patent is hereby corrected as shown below:

At Column 8, line 15:

A. Delete Claim 1 and replace it with:

1. A device which is, in combination, a drink coaster and air freshener, adapted to be positioned in a drink holder or on a flat surface, comprising a substantially circular or polygonal shaped disk, said disk further comprising a plurality of layers including a liquid absorbent top layer and a bottom layer and an air freshener middle layer impregnated with a material capable of evaporation and selected from a group of substances or mixtures having an odor pleasing to humans or capable of combating odors unpleasant to humans.

At column 8, line 30:

B. Delete claim 3 and replace it with:

3. The Device of Claim 1, wherein the layers of the disk beneath the top layer are smaller in circumference than the top layer, whereby spilled liquid is less likely to contact the middle and bottom layer of the disk or the bottom of said drink holder.

UNITED STATES PATENT AND TRADEMARK OFFICE
CERTIFICATE OF CORRECTION

| | |
|---|---|
| PATENT NO. | : 6,695,272 B1 |
| APPLICATION NO. | : 10/080227 |
| DATED | : February 24, 2004 |
| INVENTOR(S) | : Bomgaars et al. |

It is certified that error appears in the above-identified patent and that said Letters Patent is hereby corrected as shown below:

At column 8, lines 36-45

C. Delete claim 4 and replace it with:

4. The device of Claim 1, wherein the top layer includes one or more sets of substantially circular or polygonal lines of perforations or lines of weakness, inside of, and parallel to, the circumference of said disk, whereby an outer substantially ring-shaped portion of the top layer of said disk can be removed by tearing outer portions of the top layer away from the inside substantially circular or polygonal shaped portion of said disk, and whereby the diameter of said disk can be changed to fit drink holders of varying sizes.

D. Delete claim 5 and replace it with:

5. The device of Claim 1, wherein the air freshener layer impregnated with a material capable of evaporation, has an exposed substantially cylindrical or polygonal edge surface out of which the material can evaporate from the disk, and wherein the top and bottom surfaces of said air freshener layer are sealed by being attached to one or more layers of liquid impervious material.

UNITED STATES PATENT AND TRADEMARK OFFICE
CERTIFICATE OF CORRECTION

| | | |
|---|---|---|
| PATENT NO. | : 6,695,272 B1 | Page 3 of 13 |
| APPLICATION NO. | : 10/080227 | |
| DATED | : February 24, 2004 | |
| INVENTOR(S) | : Bomgaars et al. | |

It is certified that error appears in the above-identified patent and that said Letters Patent is hereby corrected as shown below:

At column 8, lines 46-67:

E. Delete claim 6 and replace it with:

6. The device of Claim 5, wherein the liquid impervious layer comprises waxed paper, plastic, a continuous coating of glue, or a continuous coating of adhesive, or a layer of plastic applied by spraying the plastic dissolved in a solvent capable of evaporation.

F. Delete claim 7 and replace it with:

7. The device of Claim 1, wherein the liquid absorbent top layer comprises cardboard, pulp board, blotter paper, pulp paper, natural sponge, plastic foam, or matted fibers.

G. Delete claim 8 and replace it with:

8. The device of Claim 5, wherein the air freshener layer is comprised of cardboard, pulp board, blotter paper, pulp paper, natural sponge, plastic foam, or matted fibers.

H. Delete claim 9 and replace it with:

9. The device of Claim 1, wherein the bottom layer, beneath the air freshener layer, is comprised of substantially the same material as the liquid absorbent top layer.

UNITED STATES PATENT AND TRADEMARK OFFICE
CERTIFICATE OF CORRECTION

PATENT NO.        : 6,695,272 B1
APPLICATION NO.   : 10/080227
DATED             : February 24, 2004
INVENTOR(S)       : Bomgaars et al.

It is certified that error appears in the above-identified patent and that said Letters Patent is hereby corrected as shown below:

At column 9, lines 1-20:

I. Delete claim 10 and replace it with:

10. The device of Claim 3, further comprising a removal hole in the disk positioned relatively close to the edge of the disk and adapted for insertion of a pointed object, whereby the disk is capable of being easily removed by the pointed object from said drink holder.

J. Delete claim 11 and replace it with:

11. The device of Claim 4, further comprising a removal hole in the disk positioned relatively close to the edge of the disk but inside the set of perforations or lines of weakness with the smallest diameter, and adapted for insertion of a pointed object, whereby the disk is capable of being easily removed by the pointed object from said drink holder.

K. Delete claim 12 and replace it with:

12. The device of Claim 5, further comprising a removal hole in the disk positioned relatively close to the edge of the disk and adapted for insertion of a pointed object, whereby the disk is capable of being easily removed by the pointed object from said drink holder.

UNITED STATES PATENT AND TRADEMARK OFFICE
CERTIFICATE OF CORRECTION

| | |
|---|---|
| PATENT NO. | : 6,695,272 B1 |
| APPLICATION NO. | : 10/080227 |
| DATED | : February 24, 2004 |
| INVENTOR(S) | : Bomgaars et al. |

It is certified that error appears in the above-identified patent and that said Letters Patent is hereby corrected as shown below:

At column 9, lines 21-33:

L. Delete claim 13 and replace it with:

13. The device of Claim 2, wherein the layers of the disk beneath the top layer are smaller in circumference than the top layer, whereby spilled liquid from a drink container is less likely to contact the middle and bottom layer of the disk or the bottom of the drink holder.

M. Delete claim 14 and replace it with:

14. The device of Claim 4, wherein the layers of the disk beneath the top layer are smaller in circumference than the top layer, whereby spilled liquid from a drink container is less likely to contact the middle and bottom layer of the disk or the bottom of the drink holder.

N. Delete claim 15 and replace it with:

15. The device of Claim 5, wherein the layers of the disk beneath the top layer are smaller in circumference than the top layer, whereby spilled liquid from a drink container is less likely to contact the middle and bottom layer of the disk or the bottom of the drink holder.

UNITED STATES PATENT AND TRADEMARK OFFICE
CERTIFICATE OF CORRECTION

PATENT NO. : 6,695,272 B1
APPLICATION NO. : 10/080227
DATED : February 24, 2004
INVENTOR(S) : Bomgaars et al.

It is certified that error appears in the above-identified patent and that said Letters Patent is hereby corrected as shown below:

At column 9, lines 34-57:

O. Delete claim 16 and replace it with:

16. The device of Claim 4, further comprising a logo, symbol, name, or other advertising or identifying mark printed or embossed on the liquid absorbent top layer of said disk.

P. Delete claim 17 and replace it with:

17. The device of Claim 5, further comprising a logo, symbol, name, or other advertising or identifying mark printed or embossed on the liquid absorbent top layer of said disk.

Q. Delete claim 18 and replace it with:

18. The device of Claim 9, further comprising a logo, symbol, name, or other advertising or identifying mark printed or embossed on the liquid absorbent top layer of said disk.

UNITED STATES PATENT AND TRADEMARK OFFICE
CERTIFICATE OF CORRECTION

| | |
|---|---|
| PATENT NO. | : 6,695,272 B1 |
| APPLICATION NO. | : 10/080227 |
| DATED | : February 24, 2004 |
| INVENTOR(S) | : Bomgaars et al. |

It is certified that error appears in the above-identified patent and that said Letters Patent is hereby corrected as shown below:

At column 9, lines 57-59:

R. Delete claim 19 and replace it with:

19. The device of Claim 4, further comprising a removal hole in the disk positioned relatively close to the edge of the disk but inside the set of perforations or lines of weakness with the smallest diameter, and adapted for insertion of a pointed object, whereby the disk is capable of being easily removed by the pointed object from a drink holder, and wherein the layers of the disk beneath the top layer are smaller in circumference than the top layer.

UNITED STATES PATENT AND TRADEMARK OFFICE
CERTIFICATE OF CORRECTION

| | |
|---|---|
| PATENT NO. | : 6,695,272 B1 |
| APPLICATION NO. | : 10/080227 |
| DATED | : February 24, 2004 |
| INVENTOR(S) | : Bomgaars et al. |

It is certified that error appears in the above-identified patent and that said Letters Patent is hereby corrected as shown below:

At column 9, lines 60-63:

S. Delete claim 20 and replace it with:

20. The device of Claim 5, wherein the top layer includes one or more sets of substantially circular or polygonal lines of perforations or lines of weakness, inside of, and parallel to, the circumference of said disk, whereby an outer substantially ring-shaped portion of the top layer of said disk can be removed by tearing outer portions of the top layer away from the inside substantially circular or polygonal shaped portion of said disk, and whereby the diameter of said disk can be changed to fit drink holders of varying sizes, and further comprising a removal hole in the disk positioned relatively close to the edge of the disk but inside the set of perforations or lines of weakness with the smallest diameter, and adapted for insertion of a pointed object, whereby the disk is capable of being easily removed by the pointed object from a drink holder, and wherein the layers of the disk beneath the top layer are smaller in circumference than the top layer.

UNITED STATES PATENT AND TRADEMARK OFFICE
CERTIFICATE OF CORRECTION

PATENT NO. : 6,695,272 B1
APPLICATION NO. : 10/080227
DATED : February 24, 2004
INVENTOR(S) : Bomgaars et al.

It is certified that error appears in the above-identified patent and that said Letters Patent is hereby corrected as shown below:

At column 9, line 64 through column 10 line 10:

T. Delete claim 21 and replace it with:

21. A device which is, in combination, a drink coaster and air freshener, adapted to be positioned in a drink holder, comprising a substantially circular or polygonal shaped disk, said disk further comprising:

(a) a liquid absorbent means, (b) an air freshener means, (c) an air freshener holder means, (d) a diameter reducing means, (e) a disk removal means, and (f) an attaching means for attaching parts (a) and (c) together.

U. Delete claim 22 and replace it with:

22. The device of claim 1, further comprising a coaster holder comprising:

(a) a round or polygonal shaped coaster holder disk having a raised rim, adapted to hold the coaster and air freshener, and (b) a plurality of coaster retainer means extending from the raised rim of the coaster holder over the coaster and air freshener, and adapted to retain the coaster and air freshener in a fixed position in the coaster holder disk.

UNITED STATES PATENT AND TRADEMARK OFFICE
CERTIFICATE OF CORRECTION

| | |
|---|---|
| PATENT NO. | : 6,695,272 B1 |
| APPLICATION NO. | : 10/080227 |
| DATED | : February 24, 2004 |
| INVENTOR(S) | : Bomgaars et al. |

It is certified that error appears in the above-identified patent and that said Letters Patent is hereby corrected as shown below:

At column 10 lines 11-16:

V. Delete claim 23 and replace it with:

23. The device of claim 22, further comprising a coaster holder hole through said holder, and a removal hole in the raised rim of the holder, whereby a human finger or other elongate object can move through the coaster holder hole and press the coaster and air freshener out from the coaster holder, and whereby a pointed object can be inserted in the removal hole, whereby the coaster holder can be removed from a drink holder or similar cavity.

W. Delete claim 24 and replace it with:

24. The device of claim 21, further comprising a coaster holder comprising:

(a) a round or polygonal shaped coaster holder disk having a raised rim, adapted to hold the coaster and air freshener, and (b) a plurality of coaster retainer means extending from the raised rim of the coaster holder over the coaster and air freshener, and adapted to retain the coaster and air freshener in a fixed position in the coaster holder.

UNITED STATES PATENT AND TRADEMARK OFFICE
CERTIFICATE OF CORRECTION

PATENT NO. : 6,695,272 B1
APPLICATION NO. : 10/080227
DATED : February 24, 2004
INVENTOR(S) : Bomgaars et al.

It is certified that error appears in the above-identified patent and that said Letters Patent is hereby corrected as shown below:

At column 10 lines 17-44:

X. Delete claim 25 and replace it with:

25. The device of claim 24, further comprising a coaster holder hole through said holder, and a removal hole in the raised rim of the holder, whereby a human finger or other elongate object can move through the coaster holder hole and press the coaster and air freshener out from the coaster holder, and whereby a pointed object can be inserted in the removal hole, whereby the coaster holder can be removed from a drink holder or similar cavity.

Y. Delete claim 26 and replace it with:

26. The device of claim 23, wherein the coaster holder is made of plastic comprising a glow in the dark means.

Z. Delete claim 27 and replace it with:

27. The device of claim 25, wherein the coaster holder is made of plastic comprising a glow in the dark means.

UNITED STATES PATENT AND TRADEMARK OFFICE
CERTIFICATE OF CORRECTION

| | | |
|---|---|---|
| PATENT NO. | : 6,695,272 B1 | |
| APPLICATION NO. | : 10/080227 | |
| DATED | : February 24, 2004 | |
| INVENTOR(S) | : Bomgaars et al. | |

It is certified that error appears in the above-identified patent and that said Letters Patent is hereby corrected as shown below:

At column 10, lines 45-46:

AA. Delete claim 28 and replace it with:

28. The device of claim 23, wherein the coaster holder is made of plastic or other moldable material, impregnated with air freshener means, and wherein the air freshener layer is absent.

At column 10, lines 47-64

BB. Delete claim 29 and replace it with:

29. A device which is, in combination, a drink coaster and air freshener, adapted to be positioned in a drink holder, comprising a substantially circular or polygonal shaped disk, said disk further comprising:

UNITED STATES PATENT AND TRADEMARK OFFICE
CERTIFICATE OF CORRECTION

| | | |
|---|---|---|
| PATENT NO. | : 6,695,272 B1 | Page 13 of 13 |
| APPLICATION NO. | : 10/080227 | |
| DATED | : February 24, 2004 | |
| INVENTOR(S) | : Bomgaars et al. | |

It is certified that error appears in the above-identified patent and that said Letters Patent is hereby corrected as shown below:

(a) a liquid absorbent means, (b) a dimaeter reducing means, (c) a disk removal means, and further comprising a coaster holder comprising:

(d) a round or polygonal shaped coaster holder disk having a raised rim, adapted to hold the coaster and air freshener, and (e) a plurality of coaster retainer means extending from the raised rim of the coaster holder over the coaster and air freshener, and adapted to retain the coaster and air freshener in a fixed position in the coaster holder, wherein the coaster holder disk is comprised of plastic or other moldable material, impregnated with air freshener means.

Signed and Sealed this

Nineteenth Day of September, 2006

JON W. DUDAS
*Director of the United States Patent and Trademark Office*